United States Patent [19]

Avar et al.

[11] Patent Number: 4,891,396
[45] Date of Patent: Jan. 2, 1990

[54] NEW BENZTRIAZOLYL COMPOUNDS

[75] Inventors: Lajos Avar, Biel-Benken, Switzerland; Helmut Böhnke, Bad, Fed. Rep. of Germany

[73] Assignee: Sandoz Ltd., Basel, Switzerland

[21] Appl. No.: 237,122

[22] Filed: Aug. 26, 1988

[30] Foreign Application Priority Data

Aug. 28, 1987 [GB] United Kingdom ................ 8720365

[51] Int. Cl.$^4$ ...................... C07D 249/20; C08K 5/34
[52] U.S. Cl. ..................................... 524/91; 548/259; 524/99
[58] Field of Search ................. 524/91, 99; 548/259, 548/260, 261

[56] References Cited

U.S. PATENT DOCUMENTS

| | | | |
|---|---|---|---|
| 3,189,615 | 6/1965 | Heller et al. | 548/260 |
| 3,766,205 | 10/1973 | Heller et al. | 548/261 |
| 3,978,074 | 8/1976 | Jancis | 548/260 |
| 4,220,788 | 9/1980 | Bader et al. | 548/259 |
| 4,727,158 | 2/1988 | Seltzer et al. | 548/260 |

Primary Examiner—Veronica P. Hoke
Attorney, Agent, or Firm—Gerald D. Sharkin; Richard E. Vila; Thomas C. Doyle

[57] ABSTRACT

A compound of formula I

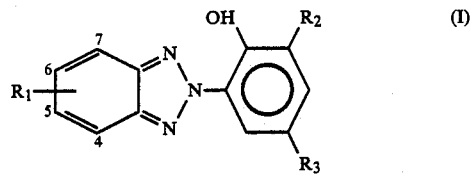

in which $R_1$ is selected from $C_{9-32}$alkyl, $C_{9-32}$alkenyl, $C_{9-32}$alkoxy, $-CO-R_4$ and $-(CH_2)_{1-6}-COOC_{6-18}$alkyl, where $R_4$ is $C_{8-31}$alkyl, $C_{8-31}$alkenyl or $C_{8-31}$alkoxy; the alkyl group of each significance of $R_1$ being uninterrupted or interrupted by one $-O-$, $-S-$ $-SO_2-$ group and being unsubstituted or substituted by $-N(R_5)_2$, OH or halogen, where each $R_5$, independently, is selected from hydrogen, $C_{1-6}$alkyl, $C_{2-6}$alkenyl and $C_{1-6}$alkoxy;

$R_2$ has a significance of $R_1$ independently, of $R_1$ or is $-COOH$ hydrogen, hydroxy$C_{1-6}$alkyl, hydroxy$C_{1-6}$alkoxy, $-COOC_{1-6}$alkyl, $OCOC_{1-6}$alkoxy; Cl, Br, I, OH, $C_{1-8}$alkyl, $C_{1-8}$alkoxy or $C_{2-8}$alkenyl; and $R_3$ is $C_{1-6}$alkyl, Cl, Br, I, OH, COOH, hydroxy$C_{1-6}$alkyl, $C_{2-6}$alkenyl, hydroxy$C_{1-6}$alkoxy, $COOC_{1-6}$alkyl, $-OCOC_{1-6}$alkoxy or $C_{1-32}$alkoxy provided that when $R_2$ contains more than six carbon atoms, $R_3$ contains six or less carbon atoms.

These compounds are useful as U.V. absorbers in polymeric systems.

24 Claims, No Drawings

NEW BENZTRIAZOLYL COMPOUNDS

This invention relates to new benztriazolyl compounds that are useful as U.V. absorbers.

According to the invention, there is provided a compound of formula I

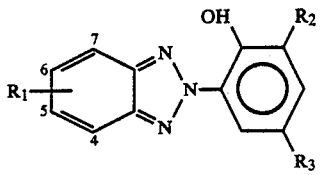

in which $R_1$ is selected from $C_{9-32}$alkyl, $C_{9-32}$alkyenyl, $C_{9-32}$alkoxy, —CO—$R_4$ and —$(CH_2)_{1-6}$—COOC$_{6-18}$alkyl, where $R_4$ is $C_{8-31}$alkyl, $C_{8-31}$alkenyl or $C_{8-31}$alkoxy; the alkyl group of each significance of $R_1$ being uninterrupted or interrupted by one —O—, —S— or —SO$_2$— group and being unsubstituted or substituted by —N($R_5$)$_2$, OH or halogen, where each $R_5$, independently, is selected from hydrogen, $C_{1-6}$alkyl, $C_{2-6}$alkenyl and $C_{1-6}$alkoxy;

$R_2$ has a significance of $R_1$, independently of $R_1$, or is —COOH, hydrogen, hydroxy$C_{1-6}$alkyl, hydroxy$C_{1-6}$alkoxy, —COOC$_{1-6}$alkyl, OCOC$_{1-6}$alkoxy; Cl, Br, I, OH, $C_{1-8}$alkyl, $C_{1-8}$alkoxy or $C_{2-8}$alkenyl; and $R_3$ is $C_{1-6}$alkyl, Cl, Br, I, OH, COOH, hydroxy$C_{1-6}$alkyl, $C_{2-6}$alkenyl, hydroxy$C_{1-6}$alkoxy, COOC$_{1-6}$alkyl, —OCOC$_{1-6}$-alkoxy or $C_{1-32}$alkoxy provided that when $R_2$ contains more than six carbon atoms, $R_3$ contains six or less carbon atoms.

Preferably, $R_1$ is in the 5-position as shown in formula I.

Any long chain groups present may exist in isomeric form. Compounds of formula I include mixtures thereof.

The compounds according to the invention are preferably in liquid form at room temperature (25° C.) and normal pressure (1 atmosphere).

Preferably, $R_1$ is $R_1'$ where $R_1'$ is $C_{9-22}$alkyl, $C_{9-22}$alkenyl or $C_{9-22}$alkoxy. More preferably, $R_1$ is $R_1''$ where $R_1''$ is $C_{9-18}$alkyl. Most preferably $R_1$ is $R_1'''$ where $R_1'''$ is $C_{9-14}$alkyl. $R_1$ is especially $C_{12}H_{25}$.

Preferably $R_2$ is $R_2'$ where $R_2'$ is hydrogen, $C_{1-22}$alkyl, $C_{2-22}$alkenyl or $C_{1-22}$alkoxy. More preferably $R_2$ is $R_2''$ where $R_2''$ is $C_{1-22}$alkyl. Most preferably $R_2$ is $R_2'''$ where $R_2'''$ is $C_{6-18}$alkyl. $R_2$ is especially $C_8H_{17}$ or $C_{12}H_{25}$.

Preferably $R_3$ is $R_3'$ where $R_3'$ is $C_{1-6}$alkyl, $C_{1-6}$alkoxy or $C_{2-6}$alkenyl. More preferably $R_3$ is $R_3''$ where $R_3''$ is $C_{1-6}$alkyl, most preferably $R_3$ is $R_3'''$ where $R_3'''$ is $C_{1-4}$alkyl, especially methyl or t-butyl.

Further, according to the invention there is provided a polymeric composition comprising a polymeric material and a compound of formula I.

Preferably such a polymeric composition is a lacquer composition based on an acrylic, alkyd, polyester and/or polyurethane resin.

Further, according to the invention, there is provided a composition comprising a compound of formula I and a hindered amine light stabiliser, preferably an N-unsubstituted, N-alkyl or N-acyl substituted 2,2,6,6-tetramethylpiperidine compound.

Preferred hindered light stabilisers are those described in British Published Patent Application 2,136,805 A; 2,180,537 A and 2,176,482 A and British Patent 2,089,800 B; Belgian Patent 853,476; European Patents 52 579, 52 073 and U.S. Pat. No. 4,198,334 the conttents and preferences of which are incorporated herein by reference.

Compounds of formula I together with a hindered amine light stabiliser in a polymeric composition according to the invention may exhibit synergism in the polymeric composition.

Further, according to the invention, there is provided a method for preparing a compound of formula I comprising reducing and cyclising the compound of formula II

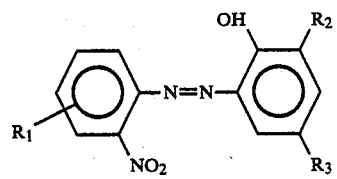

where the symbols are as defined above, at room or elevated temperature.

Preferably the reducing and cyclising agent is zinc dust.

The concentration of compound of formula I employed in the polymeric material is suitably 0.01 to 8% by weight, preferably 0.02% to 4% by weight of polymeric material. The compound may be added before, during or after the polymerization step, and may be added in solid form in solution, preferably as a liquid concentrate containing from 20 to 80% by weight of compound of formula I, or as a solid masterbatch composition containing 20 to 80% by weight of compound of formula I and 80 to 20% by weight of a solid polymeric material which is identical with or compatible with the polymeric material to be stabilized. When the compound of formula I is in liquid form it can be used as the liquid without any further additions.

Suitable polymeric materials include plastic materials for example polyethylene, polypropylene, ethylene/propylene copolymes, polyvinyl chloride, polyester, polyamide, polyurethane, polyacrylonitrile, ABS, terpolymers of acrylates, styrene and acrylonitrile, styrene/acrylonitrile and styrene/butadiene. Other plastics materials such as polybutylene, polystyrene, chlorinated polyethylene, polycarbonate, polymethylmethacrylate, polyphenylene oxide, polypropylene oxide, polyacetals, phenol/formaldehyde resins and epoxy resins may also be used. Preferred plastic materials are polypropylene, polyethylene, ethylene/propylene copolymers and ABS. Natural polymers for example natural rubber may also be stabilized, as may lubricating oils containing polymeric material.

The compounds of formula I may be incorporated by known methods into the polymeric material to be stabilized. Of particular importance is blending of the compounds with thermoplastic polymers in the melt, for example in a melt blender or during the formation of shaped articles, including foils, films, tubes, containers, bottles, fibres and foams by extrusion, injection moulding, blow moulding, spinning or wire coating.

It is not essential for the polymeric material to be fully polymerised before mixing with the compound according to the invention. The compounds may be mixed with monomer, prepolymer or precondensate, and the polymerisation or condensation reaction carried out subsequently. This will of course be the peferred method of incorporation of the compounds into thermosetting polymers, which cannot be melt blended.

The compounds of formula I may be used alone or in combination with other stabilizers, for example antioxidants. Examples include sterically hindered phenols, sulphur or phosphorus-containing compounds or mixtures of these. Examples are benzofuran-2-ones, indolin-2-ones and sterically hindered phenols such as beta-(4-hydroxy-3,5-ditert.butylphenyl)-propionyl stearate, methane tetrakis-(methylene-3 (3',5'-ditert.butyl-4-hydroxy-phenyl)propionate), 1,3,3-tris-(2-methyl-4-hydroxy-5-tert.butyl phenyl)butane, 1,3,5-tris (4-tert.butyl-3-hydroxy-2,6-di-methylbenzyl)-1,3,5-triazinyl-2,4,6 (1H, 3H, 5H)-trione, bis-(4-tert.butyl-3-hydroxy-2,6-di-methylbenzyl)dithiolterephthalate, tris (3,5-ditert.butyl-4-hydroxybenzyl) isocyanurate, the triester of beta-(4-hydroxy-3,5-ditert.-butylphenyl) propionic acid with 1,3,4-tris-(2-hydroxyethyl)-5-triazinyl-2,4,6 (1H, 3H, 5H)-trione, bis (3,3-bis-(4'-hydroxy-3'-tert.butylphenyl)-butyric acid) glycol ester, 1,3,5-trimethyl-2,4,6-tris-(3,5-ditert.butyl-4-hydroxy-benzyl) benzene, 2,2'-methylene-bis-(4-methyl-6-tert.butylphenyl) terephthalate, 4,4-methylene-bis-(2,6-ditert.-butyl-phenol), 4,4'-butylidine-bis-(tert.butylmetacresol), 2,2'-methylene-bis-(4-methyl-6-tert.butyl)-phenol.

Sulphur containing antioxidative co-stabilizers which may be used include for example distearylthiodipropionate, di-laurylthiodipropionate, methane tetrakis (methylene-3-hexylthiopropionate), methane tetrakis (methylene-3-dodecylthiopropionate) and dioctadecyl-disulphide. Phosphorus-containing co-stabilizers include for example trinonylphenyl phosphite, 4,9-distearyl-3,5,8,10-tetraoxadiphosphaspiroundecane, tris-(2,4-ditert.butylphenyl)phosphite and tetrakis (2,3-ditert.-butylphenyl)-4,4'-biphenylene diphosphonite. Further additives such as aminoaryl compounds and U.V.-absorbers and light stabilizers e.g. 2-(2'-hydroxyphenyl)benzotriazole, 2-hydroxy-benzophenone, 1,3-bis-(2'-hydroxybenzoyl)benzene, salicylates, cinnamates, benzoates and substituted benzoates, sterically hindered amines and oxalic acid diamides may be used. Other known types of additives, e.g. flame retardants and antistatic agents, may also be added.

The compounds of the invention can also be used in photopolymeric subtrates containing photoinitiators for the photopolymerisation.

The compounds of formula I are especially suitable for use in organic polymer-containing coatings, particularly automotive finishes.

Automotive finishes are generally solutions or dispersions of organic polymers or polymer precursors in organic solvents. The majority are stoving finishes, which require the application of heat, generally above 80° C., in order to harden the finish in an acceptable time once it has been applied to the primer coated metal surface. The hardening step may be accelerated by the use of an acid catalyst. The effect of this heating may be to accelerate the chemical reaction between polymer precursors in a thermosetting system, or to bring about fusion of particles of a thermoplastic polymer.

Many automative finishes are metallic finishes, which contain flakes of metal, usually aluminium, in order to provide optical effects due to reflection. Such finishes are often two-coat finishes, in which a clear top coat finish is applied over a base coat finish containing a single pigment and/or metal metal flakes. The compounds of formula I can be in the top coat finish or the ground coat finish, preferably the former. Such two-coat metallic finishes have particular need of U.V.-stabilizers in the top coat, since the polymer in this coat is not protected by light-absorbing pigments, and it is subjected to almost double the normal amount of radiation because of reflection of light from the lower metallic layer.

The compounds of formula I are suitable for use as U.V.-stabilizers in a wide range of liquid finishes, for example those based on combinations of melamine-formaldehyde resins with oil-modified polyester resins, polyacrylate resins with added crosslinkers, or saturated polyesters; or on self-crosslinkers, or saturated polyesters; or on self-crosslinked polyacrylate or polyacrylate resin co-polymerised with styrene.

Further examples are two-component finishes based on an aliphatic or aromatic di-isocyanate and a hydroxy-group-containing polyacrylate, polyester or polyether resin. These polyurethane 2-component finishes are preferably hardened at 60° to 120° C. Thermoplastic polyacrylate resins may also be used, the latter being particularly useful in metallic finishes, as are also polyacrylate resins with added crosslinkers in combination with melamine-formaldehyde resins etherified with butanol and, further, hydroxy-group-containing polyacrylate resins hardened with aliphatic di-isocyanates. Such polyacrylate resins are described in U.S. Pat. No. 3,062,753, the contents of which are incorporated herein by reference.

The compounds of formula I are particularly useful in acid catalysed stoving finishes particularly in the top coat of two metallic finishes.

The compounds of formula I may be added to the finish at any stage in its manufacture, and may be added in solid form or in solution, preferably in the form of a liquid concentrate in a suitable solvent or in the form of a dispersion in water or organic solvent or when a liquid, as the liquid.

In practice the compounds of formula I are added to a finish as a solution in organic solvent (as a liquid finish) in which the binder material is between 35% (low solid finishes) and 70% by weight (high solid finishes). The binder material of the finish can be in aqueous emulsion or suspension form (as an aqueous finish) in which the binder material part makes up 20 to 30% by weight. However, the compounds of formula I can be added to known powder finishes.

The compounds of formula I to be added to the liquid or powder finishes before stoving or hardening. Preferably the compounds of formula I are used in liquid finishes or when liquid just as the liquid since it is easy to add exact dosages. It is particularly preferred to use a concentrate (preferably in a hydrocarbon solvent) containing at least 40% preferably 60 to 80% by weight of the total weight of the concentrate of a compound of formula I to introduce the compound of formula I to finishes for stoving.

The additiion of from 0.01 to 8% by weight, preferably 0.2 to 4% by weight of one or more compounds of formula I gives a clear improvement in the light- and weather-stability of organic pigments in stoving finishes as well as reducing the tendency to hairline cracking and loss of gloss as the result of weathering. This is also found for metallic finishes and excellent long-term stability of the clear top coat of two layer metallic finishes is obtained. In such finishes, the compound of formula I may be added to the metallic undercoat, the clear top coat or both, preferably only to the clear top coat. The metal surface to be finished may be under-coated with primer coatings as is customary in the art of coating metal surfaces.

The invention will now be illustrated by the following Examples in which all parts and percentages are by weight and all temperatures are in degrees Centigrade.

EXAMPLE 1

(a) Preparation of 4-n-dodecyl-2-nitro-2'-hydroxy-5'-methyl-azo benzene;

30.6 g of 2-nitro-4n-dodecylaniline are added to 10 ml of water and 35 ml of toluene and then reacted with 25 ml of concentrated hydrochloric acid and then stirred at 50° C. for ½ an hour. The temperature is then reduced to −5° C. and then the product is diazotised with 7.2 g of sodium nitrite dissolved in 10 ml of water. The reaction is allowed to react for 1 hour whilst adding 50 ml of ethanol. This mixture is slowly added to a mixture of 9.0 g of p-cresol, 12,4 g of NaOH, 300 ml of ethanol and 50 ml of water at 0° C., whilst stirring. After reacting for 3 hours, the reaction mixture is acidified by the addition of conc. HCl solution until the mixture is slightly acid. The aqueous phas is then extracted 3 times with toluene, the organic phase are then added together and then washed neutral. After distilling of the solvent and after chromatographic purification, 19 g of the solid product result (=54% of theory), having a melting point of 78°–79° C.

(b) Preparation of 5-n-dodecyl-2-[2'-hydroxy-5'-methyl-phenyl]-2H-benztriazole.

A solution of 28 g of 4-n-dodecyl-2-nitro-2'-hydroxy-5'-methyl-azobenzene (prepared as in part a) above) in 22 ml of water and 220 ml of isopropanol is reacted with 26 ml of 30% NaOH and warmed to 45° C. 20 g of zinc dust is added portionwise over 2 hours. The suspension is stirred at 75° C. overnight, cooled and the isopropanol solution is decanted from the zinc. The organic phase is then added to 300 ml of water and brought to pH 4 by addition of concentrated hydrochloric acid. The product is then taken up in 200 g of hexane and the hexane phase is washed neutral. The solvent is distilled off under vacuum and the product is chromatographically purified. The resulting product is white.

EXAMPLE 2

(a) By a method analogous to that of Example 1a, 24.9 g of 2-nitro-4-n-dodecylaniline can be diazotised and reacted with 18.7 g of 2-sec.-dodecyl-4-methyl-phenol to produce 4-n-dodecyl-2-nitro-3'-sec.-dodecyl-2'-hydroxy-5'-methyl-azobenzene which is a red solid product, having a melting point of 56°–58° C.

(b) By a method analogous with that of Example 1b, 39 g of 4-n-dodecyl-2-nitro-3'-sec.-dodecyl-2'-hydroxy-5'-methyl azobenzene (produced as in part a) above) is converted to 5-n-dodecyl-2-[2'-hydroxy-3'-sec.-dodecyl-5'-methyl-phenyl]-2H-benztriazole which is a orange oil.

EXAMPLE 3

Preparation of 5-dodecyl-2-[2'-hydroxy-5'-methyl-3'-octyl-phenyl]-2H benztriazole.

20 g of the product of Example 1b is stirred for 6 hours in the presence of 3.3 ml of methane sulphonic acid an excess of octene at 120° C. The product is taken up in hexane, and the hexane phase is washed neutral. After chromatographic purification a non-crystalline oil results which is 5-dodecyl-2-[2'-hydroxy-5'-methyl-3'-octyl-phenyl]-2H benztriazole.

The 5-dodecyl group in the Example 3 is an isomeric mixture of sec.-dodecyl annd n-dodecyl, since isomerisation of the n-dodecyl group occurs to about 50:50.

The octyl group in Example 3 is a mixture of different isomers.

EXAMPLES 4 and 5

By a method analogous with that of Example 1 compounds of the formula

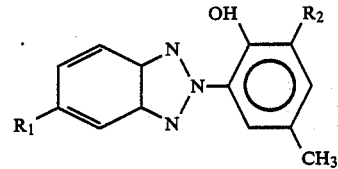

in which $R_1$ and $R_2$ are as in Table 1 below can be prepared from appropriate reactants.

TABLE

| Ex. No. | $R_1$ | $R_2$ |
|---|---|---|
| 4 | $C_{12-14}$ alkyl (isomer mix) | $C_8H_{17}$ (isomer mix) |
| 5 | $C_{12-14}$ alkyl (isomer mix) | $C_{12-14}$ alkyl (isomer mix) |

APPLICATION EXAMPLE A

80 Parts of Viacryl SC 344 (a 50% solution of an acryl resin from Vianova), 13.9 Parts of Maprenal MF 80 (a 72% solution of a melamine resin from Hoechst) and 4.1 Parts of Byketol OK (from Byk-Malinckrodt) is added to 2 parts of the benzitriazolyl product of Example 2. After 1 minute the light stabiliser material so formed is dissolved in a finish. The finish is applied conventionally (according to the known 2 layer procedure) to a metallic or single pigment finish whilst still wet by spraying to form a layer having a thickness of 30 to 40 μm. The resulting coating is then hardened at 140° for 30 minutes. The coating shows very good resistance to U.V. light and weathering.

APPLICATION EXAMPLE B

A clear finish of 29.5 Parts of Setalux C-1502 XX-60 (a 60% solution of an acryl resins from Synthese B.V.), 39.2 Parts of Setalux C-1382 BX-45 (a 45% solution of an acryl resin from Synthese B.V.), 21.4 Parts of Setamine US-138 BB-70 (a 70% solution of a melamine resin from Synthese B.V.), 2.5 Parts of Baysilonoil [(2% solution in Xylene) from Bayer] and 7.4 Parts of Depanol Y (a solvent from Hoechst) is stirred together with 2.5 parts of the benztriazolyl product of Example 2 and 2 parts of an acid catalyst derived from phosphoric acid (Type: Catalyst 269-9 from American Cyanamid) to form a homogeneous mixture. The finish is applied conventionally (according to known 2 layer procedure) to a metallic or single pigment finish whilst both are still wet by spraying to form a layer having a thickness of 30 to 40 μm. The resulting coating is then hardened at 110° for 20 minutes. The coating shows very good resistance to U.V. light and weathering.

APPLICATION EXAMPLE C

A clear finish of

75 Parts Macrynal SH 510 N (a hydroxy containing acryl resin from Bayer)
2 Parts of Baysilon-oil A [1% solution in xylene) from Bayer]
0.3 Parts of dibutyl zinc dilaurate
0.35 Parts diethanolamine
5.0 Parts of ethylglycol acetate
5.0 Parts of Solvesso 100
6.0 Parts of Xylene and
6.35 Parts of butyl acetate is added to 2.5 parts of the benztriazolyl product of Example 2 and 30 parts of Desmodur N 75 (from Bayer). The homogeneous mixture so formed is applied conventionally (according to the known 2 layer procedure) to a metallic or single pigment finish whilst both are stil wet by spraying to form a layer having a thickness of 30 to 40 μm and the resulting coating is hardened over 20 minutes at 80° to 90°. The resulting 2K-PUR coating shows a good resistance to U.V. light and weathering.

APPLICATION EXAMPLE D

A single white pigmented finish of 14.30 Parts of Setamine US-132 BB70 (a 70% solution of a melamine resin from Synthese)
57.15 Parts of Setal 84 W-70 (a 70% solution of an alkyd resin from Synthese)
7.70 Parts of n-butanol
1.85 Parts of butylglycol acetate
9.50 Parts of Xylene and
25 Parts of titanium dioxide (Rutil type)

is added with 1.38 parts of the benztriazolyl product of Example 2. The finish is conventionally applied to a grounded steel metal to which a filler of layer thickness 20 to 30 μm has been annealed, by spraying and after standing for 30 minutes at room temperature the steel metal surface is annealed at 120° C. for 30 minutes. The resulting coating shows very good resistance to U.V. light and weathering. In Application Examples A to D instead of the benztriazolyl product of Example 2, an appropriate amount of the benztriazolyl product of Example 1 or 3, or 4 or 5 can be used.

What is claimed is:

1. A compound of formula I

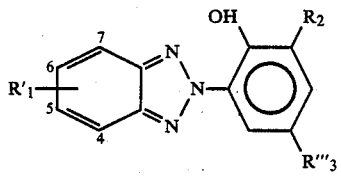

in which $R_1'$ is $C_{9-22}$alkyl, $C_{9-22}$alkenyl or $C_{9-22}$alkoxy;

$R_2$ is selected from $C_{9-32}$alkyl, $C_{9-32}$alkenyl, $C_{9-32}$alkoxy, $-CO-R_4$ and $-(CH_2)_{1-6}-COOC_{6-18}$alkyl, where $R_4$ is $C_{8-31}$alkyl, $C_{8-31}$alkenyl or $C_{8-31}$alkoxy; the alkyl group of each of the above significances of $R_2$ being uninterrupted or interrupted by one $-O-$, $-S-$ or $-SO_2$-group and being unsubstituted or substituted by $-N(R_5)_2$, OH or halogen, where each $R_5$, independently, is selected from hydrogen, $C_{1-6}$alkyl, $C_{2-6}$alkenyl and $C_{1-6}$alkoxy;

or $R_2$ is $-COOH$, hydrogen, hydroxy$C_{1-6}$alkyl, hydroxy$C_{1-6}$alkoxy, $-COOC_{1-6}$alkyl, $OCOC_{1-6}$alkoxy; Cl, Br, I, OH, $C_{1-8}$alkyl, $C_{1-8}$alkoxy or $C_{2-8}$alkenyl; and $R_3'''$ is $C_{1-4}$alkyl.

2. A compound according to claim 1, in which $R_1'$ is in the 5-position as shown in claim 1.

3. A compoud according to claim 1 in which $R_1'$ is $R_1''$ where $R_1''$ is $C_{9-18}$alkyl.

4. A compound according to claim 1 in which $R_1'$ is $R_1'''$ where $R_1'''$ is $C_{9-14}$alkyl.

5. A compound according to claim 1 in which $R_2$ is $R_2'$ where $R_2'$ is $C_{1-22}$alkyl, hydrogen, $C_{1-22}$alkenyl or $C_{1-22}$alkoxy.

6. The compound according to claim 1 which is 5-dodecyl-2-[2'-hydroxy-5'-methyl-3'-octylphenyl]-2H-benztriazole.

7. A compound according to claim 5 wherein R' is R'' where R'' is $C_{9-18}$alkyl.

8. A compound according to claim 5 wherein R' is in the 5-position.

9. A compound according to claim 7 wherein R'' is in the 5-position.

10. A compound according to claim 1 in which $R_2$ is $R_2''$ where $R_2$ is $C_{1-22}$alkyl.

11. A compound according to claim 1 in which $R_2$ is $R_2'''$ where $R_2'''$ is $C_{6-18}$alkyl.

12. The compound according to claim 1 which is 5-n-dodecyl-2-[2'-hydroxy-5'-methylphenyl]-2H-benztriazole.

13. A light stabilizing composition comprising the compound of claim 12 and a hindered amine light stabilizer.

14. The compound according to claim 1 which is 5n-dodecyl-2-[2'-hydroxy-3'-sec.-dodecyl-5'-methylphenyl]-2H-benztriazole.

15. A polymeric composition contaiñing a compound according to claim 14.

16. A light stabilizing composition comprising the compound of claim 14 and a hindered amine light stabilizer.

17. A light stabilising composition comprising a compound of formula I defined in claim 1 and a hindered amine light stabiliser.

18. A polymeric composition comprising a polymeric material and a compound according to claim 1.

19. A polymeric composition according to claim 18 comprising additionally a hindered amine light stabiliser.

20. A polymeric composition according to claim 18 which is a lacquer composition based on an acrylic, alkyd, polyester and/or polyurethane resin.

21. A composition according to claim 20 in which the amount of compound of formula I present is from 0.01 to 8% by weight of the polymeric material.

22. A composition according to claim 21 in which the compound of formula I is 5-n-dodecyl-2[2'-hydroxy-5'-methylphenyl]-2H-benztriazole.

23. A composition according to claim 21 in which the compound of formula I is 5-n-dodecyl-2-[2'-hydroxy-3'-sec.-dodecyl-5'-methylphenyl]-2H-benztriazole.

24. A composition according to claim 18 in which the amount of benztriazolyl compound of formula I present is from 0.01 to 8% by weight of the polymeric material.

* * * * *